(12) United States Patent
Roy et al.

(10) Patent No.: US 11,330,980 B2
(45) Date of Patent: May 17, 2022

(54) INDEX FOR QUANITIFICATION OF BOWMAN'S LAYER ROUGHNESS FOR DIAGNOSIS OF DISEASE AND PROGNOSIS OF TREATMENTS IN HUMAN CORNEA

(71) Applicant: Narayana Nethralaya Foundation, Bangalore (IN)

(72) Inventors: Abhijit Sinha Roy, Bangalore (IN); Rohit Shetty, Bangalore (IN); Bhujang Shetty, Bangalore (IN)

(73) Assignee: Narayana Nethralaya Foundation, Bangalore (IN)

( * ) Notice: Subject to any disclaimer, the term of this patent is extended or adjusted under 35 U.S.C. 154(b) by 369 days.

(21) Appl. No.: 16/060,807

(22) PCT Filed: Dec. 8, 2016

(86) PCT No.: PCT/IB2016/057422
§ 371 (c)(1),
(2) Date: Jun. 8, 2018

(87) PCT Pub. No.: WO2017/098424
PCT Pub. Date: Jun. 15, 2017

(65) Prior Publication Data
US 2018/0353065 A1 Dec. 13, 2018

(30) Foreign Application Priority Data

Dec. 8, 2015 (IN) .......................... 6539/CHE/2015

(51) Int. Cl.
*A61B 3/107* (2006.01)
*A61B 3/10* (2006.01)
(Continued)

(52) U.S. Cl.
CPC ............. *A61B 3/107* (2013.01); *A61B 3/0025* (2013.01); *A61B 3/102* (2013.01); *A61F 9/008* (2013.01);
(Continued)

(58) Field of Classification Search
CPC ....... A61B 3/107; A61B 3/0025; A61B 3/102; A61B 3/1015; G16H 70/60; G16H 30/20; A61F 9/008; A61F 2009/00851
(Continued)

(56) References Cited

U.S. PATENT DOCUMENTS 7,668,342 B2 * 2/2010 Everett ................ A61B 5/0066
382/106
9,278,120 B2 3/2016 Cruzat et al.
(Continued)

FOREIGN PATENT DOCUMENTS

WO 2009145842 A2 12/2009
WO 2013126602 A1 8/2013

OTHER PUBLICATIONS

Luo, Jie, Peijun Yao, Meiyan Li, Guichun Xu, Jing Zhao, Mi Tian, and Xingtao Zhou. "Quantitative analysis of microdistortions in Bowman's layer using optical coherence tomography after SMILE among different myopic corrections." Feb. 2015, Journal of Refractive Surgery 31, No. 2, 104-109. (Year: 2015).*
(Continued)

*Primary Examiner* — Serkan Akar
*Assistant Examiner* — Renee C Langhals
(74) *Attorney, Agent, or Firm* — Steven M. Koehler; Westman, Champlin & Koehler, P.A.

(57) ABSTRACT

A Bowman's Refractive Index (BRI) for quantification of microdistortions in Bowman's Layer (BL) after Small Incision Lenticule Extraction (SMILE) is defined for a patient. BRI is summation of one or more areas of the OCT image
(Continued)

of anterior edge of Bowman's layer, quantifies the smoothness of the Bowman's layer. The anterior edge of Bowman's layer is segmented into pixels. After segmentation, a $3^{rd}$ order polynomial is curve fit to the segmented pixels of the edge of Bowman's layer. BRI is calculated by segmentation of the 3-Dimensional (3-D) OCT image. BRI acts as a marker for mechanical stability and is useful for diagnosis of disease and prognosis of treatments in human.

4 Claims, 2 Drawing Sheets

(51) Int. Cl.
*A61F 9/008* (2006.01)
*A61B 3/00* (2006.01)
*G16H 30/20* (2018.01)
*G16H 70/60* (2018.01)

(52) U.S. Cl.
CPC ............ *G16H 30/20* (2018.01); *G16H 70/60* (2018.01); *A61B 3/1015* (2013.01); *A61F 2009/00851* (2013.01)

(58) Field of Classification Search
USPC .......................................................... 600/425
See application file for complete search history.

(56) References Cited

U.S. PATENT DOCUMENTS

| | | | |
|---|---|---|---|
| 9,549,966 B2 | 1/2017 | Hamrah et al. | |
| 9,560,963 B2 | 2/2017 | Buckland et al. | |
| 9,877,645 B2 | 1/2018 | Hamrah et al. | |
| 9,943,401 B2 | 4/2018 | de Juan, Jr. et al. | |
| 10,362,936 B2 | 7/2019 | Buckland et al. | |
| 10,456,030 B2 | 10/2019 | Buckland et al. | |
| 10,555,804 B2 | 2/2020 | De Juan, Jr. et al. | |
| 2007/0282313 A1* | 12/2007 | Huang | A61B 3/1005 606/5 |
| 2010/0036488 A1 | 2/2010 | de Juan, Jr. et al. | |
| 2010/0111373 A1* | 5/2010 | Chin | G06K 9/00597 382/113 |
| 2013/0336557 A1 | 12/2013 | Cruzat et al. | |
| 2014/0300862 A1* | 10/2014 | Perez | A61B 3/1005 351/206 |
| 2015/0031993 A1 | 1/2015 | Buckland et al. | |
| 2015/0038431 A1 | 2/2015 | Hamrah et al. | |
| 2015/0359426 A1 | 12/2015 | Buckland et al. | |
| 2017/0188814 A1 | 7/2017 | Hamrah et al. | |
| 2018/0035884 A1 | 2/2018 | Buckland et al. | |
| 2018/0193133 A1 | 7/2018 | De Juan, Jr. et al. | |
| 2020/0054206 A1 | 2/2020 | Buckland et al. | |

OTHER PUBLICATIONS

Abou Shousha, Mohamed, et al. "The use of Bowman's layer vertical topographic thickness map in the diagnosis of keratoconus." 2014, Ophthalmology 121.5, 988-993. (Year: 2014).*

Abou Shousha, Mohamed, et al., "The Use of Bowman's Layer Vertical Topographic Thickness Map in the Diagnosis of Keratoconus" in Ophthalmology, May 2014, pp. 988-993.

Luo, J, et al., "Quantitative Analysis of Microdistortions in Bowman's Layer using optical coherence tomography after SMILE among different myopic corrections" Feb. 2015, Abstract only.

Written Opinion for International application No. PCT/IB2016/057422, dated Feb. 23, 2017.

Examination Report in corresponding Indian Patent Application No. 6539/CHE/2015 dated Jul. 3, 2020, 6 pages.

* cited by examiner

INDEX FOR QUANITIFICATION OF BOWMAN'S LAYER ROUGHNESS FOR DIAGNOSIS OF DISEASE AND PROGNOSIS OF TREATMENTS IN HUMAN CORNEA

CROSS-REFERENCE TO RELATED APPLICATION

This Application is a Section 371 National Stage Application of International Application No. PCT/IB2016/057422, filed Dec. 8, 2016 and published as WO 2017/098424 A2 on Jun. 15, 2017, in English.

PREAMBLE TO THE DESCRIPTION

The following specification particularly describes the invention and the manner in which it is to be performed:

TECHNICAL FIELD OF THE INVENTION

The present invention defines a Bowman's Roughness Index (BRI) for quantification of microdistortions in Bowman's Layer (BL) after Small Incision Lenticule Extraction (SMILE) in patients undergoing refractive surgery. In particular, the present invention relates to the quantification of Bowman's Layer using BRI for diagnosis of diseases and prognosis of treatments in human cornea.

BACKGROUND OF THE INVENTION

Refractive surgery of the eye improves the refractive state of the eye thus reducing the necessity of contact lenses or glasses. The surgery includes various methods of remodeling of cornea. Refractive surgery is usually performed by using femtosecond (FS) lasers.

Femtosecond laser is an infrared laser that uses ultra-short pulses in the wavelength of 1053 nm for 600-800 fs. The laser works by producing photodisruption of cornea. Femtosecond laser is absorbed by the tissue resulting in plasma formation. This plasma, which is made of free electrons and ionized molecules, expands rapidly to create cavitation bubbles. The force of creation of the bubble separates the tissue. This process of conversion of laser energy into mechanical energy is termed as photodisruption.

Laser-assisted laser in situ keratomileusis (LASIK) is a femtosecond laser technology, which is most popular treatment of choice for surgical correction of refractive errors. However, LASIK is associated with microscopic tissue injury and ocular surface inflammatory mediators cause lamellar keratitis in the flap interface.

In 2011, a new method called Small Incision Lenticule Extraction (SMILE), using the FS laser is reported for complete correction of refractive error. Since then, several studies have demonstrated comparable outcomes between SMILE and LASIK. SMILE is associated with less dryness, less inflammation and better healing of the corneal wound compared to LASIK.

However, recent studies have reported the occurrence of unintended microdistortions in Bowman's layer after SMILE. The cause of these microdistortions may be multifold, e.g., ease of separation and extraction of lenticule from the stroma, corneal biomechanics, and refractive error. Bowman's layer undergoes significant reduction in thickness in case of keratoconus, indicating a biomechanically compromised stroma. The spatial thinning of the Bowman's layer is a significant indicator of keratoconus and the quantification method requires imaging of the peripheral cornea. However, in SMILE, the microdistortions are located in the central cornea and need an alternate method of quantification.

The U.S. patent application Ser. No. 14/247,903 entitled "Indices for management of dry eye syndrome, corneal ectasia, keratoplasty graft rejection and failure and Fuchs' dystrophy" discloses improved indices for the diagnosis and evaluation of conditions affecting the eye. These indices include an Enhanced Epithelial Irregularity Factor (eEIF) for the diagnosis and evaluation of conditions such as Dry Eye Syndrome (DES), Bowman's Ectasia Index (BEI), including enhanced BEI (eBEI) and BEI-Max, and Bowman's Relative Thinning (BRT) Index for the diagnosis and evaluation of ectatic conditions such as keratoconus, pellucid marginal degeneration, post-refractive surgery ectasia, and keratoglobus, and Descemet's Membrane Thickening Index (DMT), Descemet's Rejection Index (DRI), and Descemet's Membrane Irregularity Factor (DIF) for the diagnosis and evaluation of conditions, such as, keratoplasty rejection and failure and Fuchs' dystrophy incorporated into optical coherence tomography systems, or any other imaging device capable of capturing high resolution images of the cornea, for more sensitive and specific diagnosis, treatment and monitoring of certain corneal conditions. However, the invention is silent with respect to the derivation or use of any index for quantification for microdistortions in Bowman's layer.

The publication entitled "*The Use of Bowman's Layer Vertical Topographic Thickness Map in the Diagnosis of Keratoconus*" discloses the use of indices for diagnosis of keratoconus, which accurately correlated with the severity of keratoconus. Bowman's layer vertical thickness maps disclosed localized relative inferior thinning of the Bowman's layer. Bowman's layer average thickness, inferior Bowman's layer minimum thicknesses are qualitative and quantitative indices for the diagnosis of keratoconus. However, the publication is silent with respect to the microdistortions of the Bowman's layer and its quantification. The indices are predictive only for keratoconus.

The publication entitled "*Quantitative analysis of Microdistortions in Bowman's Layer using optical coherence tomography after SMILE among different myopic corrections*" discloses the quantitative analysis for characterization of Bowman's layer microdistortions after femtosecond laser Small Incision Lenticule Extraction (SMILE). The incidence and range of microdistortions in Bowman's layer detected after SMILE positively correlated with the myopic correction. High myopia tends to develop more microdistortions in Bowman's layer after SMILE. However, usually after SMILE, the microdistortions are located in the central cornea, which is a challenge for quantification. The publication is silent with respect to the quantification of microdistortions in corneal area.

Hence, there is a need to quantify the microdistortions, which is potential to cause biomechanical instability after SMILE. There is also a need for an alternative method for uniform quantification of microdistortions in cornea in the central cornea and also to monitor the biomechanical changes in cornea following SMILE.

SUMMARY OF THE INVENTION

The present invention discloses the evaluation of new index or descriptor termed as Bowman's Roughness Index for quantification of microdistortions in Bowman's layer after SMILE in patients undergoing refractive surgery.

The present invention is performed from the samples isolated from the eyes from the patient after SMILE. Bowman's layer in the central 3 mm cornea is imaged with high resolution Optical Coherence Tomography (OCT), which has an optical resolution of 2.4 µm in tissue to allow image of Bowman's layer with sufficient number of pixels.

Usually, SMILE results in microdistortions in Bowman's layer. BRI is calculated by segmentation of the 2-Dimensional (2-D) OCT image. The posterior edge of Bowman's layer is less evident after SMILE and hence the anterior edge is considered for segmentation. After segmentation, a $3^{rd}$ order polynomial is curve fit to the segmented pixels of the edge of the Bowman's layer. The areas enclosed in the Bowman's layer are termed as $A_1, A_2, A_3, \ldots A_n$ and BRI is defined as $$BRI = \Sigma_{k=1}^{n} A_k = A_1 + A_2 + \ldots + A_k$$

The magnitude of BRI is directly proportional to the number of microdistortions in Bowman's layer.

The present invention discloses the mean BRI of $1.86 \times 10^{-3} \pm 6.9 \times 10^{-5}$ mm$^2$, $2.56 \times 10^{-3} \pm 3.7 \times 10^{-5}$ mm$^2$, $3.14 \times 10^{-3} \pm 8.5 \times 10^{-5}$ mm$^2$ and $2.43 \times 10^{-3} \pm 8.5 \times 10^{-5}$ mm$^2$ before, 1 day after, 1 week after and 1 month after surgery respectively.

The present invention also discloses the calculation of BRI by segmentation of the 3-Dimensional (3-D) OCT image. BRI is also useful for 3-D mapping of the roughness of the Bowman's layer. The 3-D image is created by segmenting the surface from volume imaging or 2-D interpolated scanning BRI and by replacing the shaded areas by shaded volumes. BRI calculation in 3-D is as follows:

$$BRI = \iint (z - f(x,y)) dx dy$$

Where, (x,y,z) represent the co-ordinates of the pixels or voxels on the surface, $z' = f(x,y)$ represents 2-D interpolation method where f is the smoothing function and $z'$ are the smoothened z co-ordinates.

The present invention is useful to calculate the curvature and wave front aberrations of the different layers of the cornea using the detected edges and surface reconstruction [f(x,y)]. Wave front aberrations are calculated using techniques such as ray tracing.

The BRI defined in the present invention and method of quantification of microdistortions in Bowman's layer using BRI is useful in determining the mechanical stability of Bowman's layer and is useful for prognosis and treatment of diseases in human.

DETAILED DESCRIPTION OF THE INVENTION

In order to make the matter of the invention clear and concise, the following definitions are provided for specific terms used in the following description.

The term "Bowman's Layer" means smooth, acellular, non-regenerating layer, located between the superficial epithelium and the stroma in the cornea of the eye.

The term "Prognosis" refers to prediction of key outcome of one's current standing.

The present invention defines a Bowman's Roughness Index for quantification of microdistortions in Bowman's layer in patients undergoing SMILE for refractive surgery especially myopia. Bowman's Roughness Index is a parameter for quantification of the microdistortions in Bowman's layer and acts as a biomarker to diagnosis of the diseases in human.

Usually, SMILE results in the formation of microdistortions in Bowman's layer, which results in altered biomechanical changes. The Bowman's Roughness Index is defined by considering the anterior edge of the Bowman's layer.

The cornea samples are isolated from patients undergoing SMILE. The preliminary biomechanics of the cornea is assessed with the air-puff method. Images of the Bowman's layer in the central 3 mm layer of the cornea are acquired using high resolution spectral domain optical coherence tomography, which has a resolution of 2.4 µm in tissue to allow image of the Bowman's layer with sufficient number of pixels. The optical coherence tomography is performed along the nasal-temporal direction. The location of the 2-D scan is set at each follow-up such that it subdivided the projection image of the cornea into nearly two equal halves upon careful visual examination. Further, at least three 2-D scans are acquired in quick succession at each follow-up time point.

One month after the surgery, the parameters such as Uncorrected Distance Visual Acuity (UDVA), Corrected Distance Visual Acuity (CDVA), sphere, cylinder and corneal deformation are measured.

Figure 1:
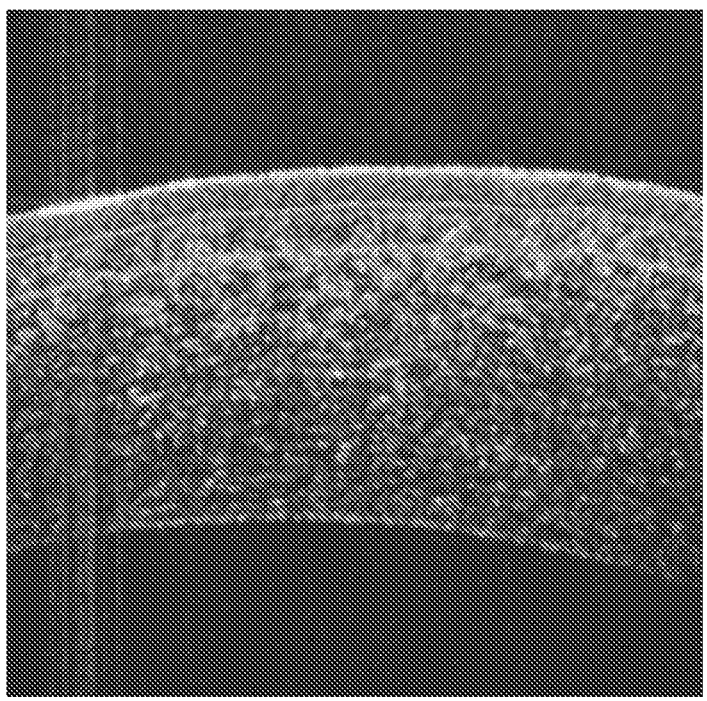
FIG. 1 illustrates the segmentation of optical coherence tomography images before and after surgery.

FIG. 1 illustrates the segmentation of optical coherence tomography images before and after surgery. After SMILE, the posterior edge of the Bowman's layer is less evident and hence only the anterior edge of the Bowman's layer is considered for further examination. The anterior edge of the Bowman's layer is segmented into number of pixels from the optical coherence tomography images before and after surgery using gradient based thresholding. After segmentation, a $3^{rd}$ order polynomial is curve fit to the segmented pixels of the Bowman's layer edge.

Figure 2:
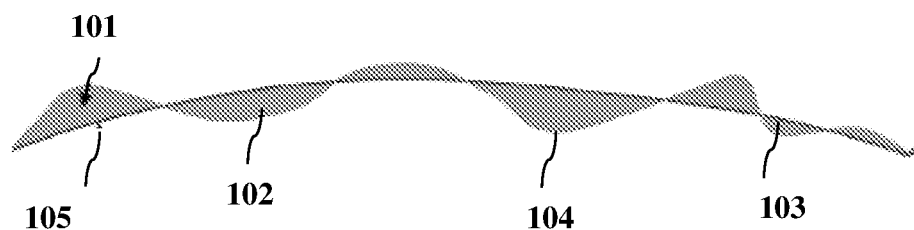
FIG. 2 illustrates the schematic overlay of the segmented edge of Bowman's layer.

FIG. 2 illustrates the schematic overlay of the segmented edge of Bowman's layer. The segmented edge of Bowman's layer and the $3^{rd}$ order polynomial curve fit to the segmented pixels of the Bowman's layer edge is used to identify the microdistortions. The areas represent the areas enclosed between the microdistortions (104) and $3^{rd}$ order polynomial curve fit (105). These areas in the segmented edge are represented as $A_1$ (101), $A_2$ (102), $A_3 \ldots A_n$ (103), where n is the number of areas enclosed.

The microdistortions in Bowman's layer are quantified using the analysis of these areas. In order to quantify the microdistortions in the Bowman's layer, a Bowman's Roughness Index is defined in the present invention. Bowman's Roughness Index is calculated based on the areas represented in the segmented edge.

Bowman's Roughness Index is defined as follows:

$$BRI = \Sigma_{k=1}^{n} A_k = A_1 + A_2 + \ldots A_k \quad (1)$$

The magnitude of Bowman's Roughness Index is directly proportional to the number of the microdistortions in the Bowman's layer i.e. if BRI value is zero, the microdistortions are absent. The mean BRI from the three images of each eye is calculated and used for further analyses.

The present invention also discloses the calculation of BRI in 3-D image. A smoothened Bowman's surface is created by segmenting the surface from volume imaging or 2-D interpolated scanning using cubic spline interpolation, multi-dimensional polynomials. The 3-D image is created by segmenting the surface from volume imaging or 2-D interpolated scanning BRI and by replacing the shaded areas by shaded volumes. BRI is calculated by segmentation of the 3-Dimensional (3-D) OCT image. BRI calculation in 3-D is as follows:

$$BRI = \iint (z - f(x,y)) dx dy$$

Where,
(x,y,z) represent the co-ordinates of the pixels or voxels on the surface,
z'=f(x,y) represents 2-D interpolation method where f is the smoothing function and z' are the smoothened z co-ordinates.

BRI is also useful for 3-D mapping of the roughness of the Bowman's layer. The present invention is useful to calculate the curvature and wave front aberrations of the different layers of the cornea using the detected edges and surface reconstruction [f(x,y)]. Wave front aberrations are calculated using techniques such as ray tracing.

Figure 3:
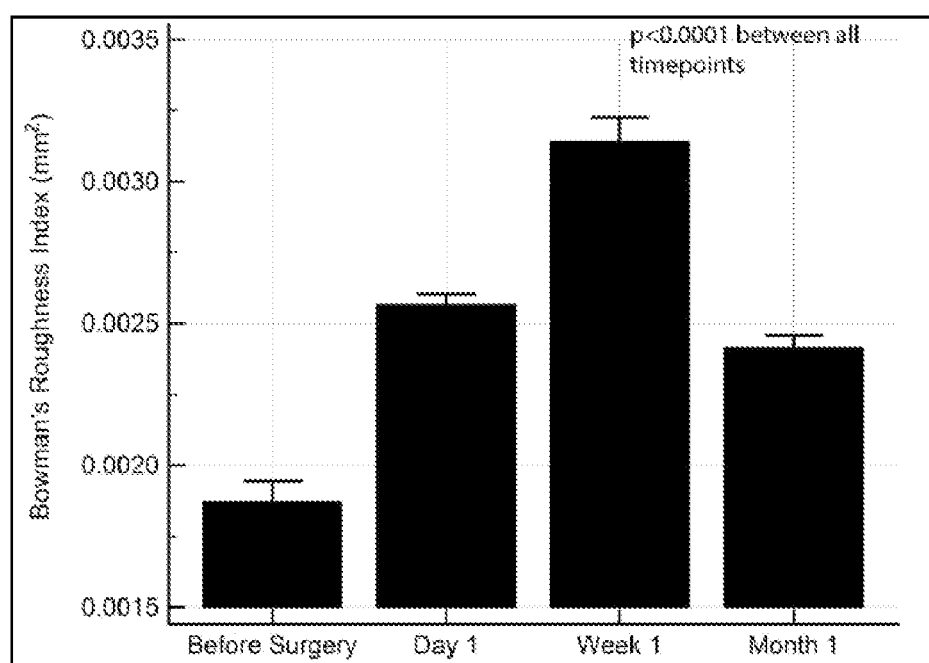
FIG. 3 illustrates the mean BRI before and after surgery.

FIG. 3 illustrates the mean BRI before and after surgery. The results showed that mean BRI is $1.86 \times 10^{-3} \pm 6.9 \times 10^{-5}$ mm$^2$, $2.56 \times 10^{-3} \pm 3.7 \times 10^{-5}$ mm$^2$, $3.14 \times 10^{-3} \pm 8.5 \times 10^{-5}$ mm$^2$ and $2.43 \times 10^{-3} \pm 8.5 \times 10^{-5}$ mm$^2$ before, 1 day after, 1 week after and 1 month after surgery, respectively. The mean ratio of post to preoperative BRI at 1 day, 1 week and 1 month after surgery is 1.40±0.04, 1.64±0.07 and 1.34±0.05, respectively. The results further showed that mean BRI before surgery is significantly different from mean BRI at day 1 (p<0.0001), week 1 (p<0.0001) and month 1 (p<0.0001). Mean BRI at week 1 is significantly different from mean BRI at day 1 (p<0.0001) and month 1 (p<0.0001) after surgery. The Co-efficient of Variation (CV) of BRI is 0.1%. The mean coefficient of regression of the 3$^{rd}$ order polynomial curve fit on segmented Bowman's layer edge is $0.99 \pm 1 \times 10^{-3}$. The mean ratio of post to preoperative BRI correlated significantly with postoperative decrease in spherical equivalent refractive error (r=+0.51, p=0.02) and with postoperative improvement in UDVA (r=+0.38, p=0.03) at 1 month.

EXAMPLE 1

The study includes the analysis of eyes of patients between 18 to 50 years of age undergoing SMILE with a stable moderate to high myopia for a minimum period of one year, a corrected distance visual acuity of 20/25 or better, a spherical equivalent refraction less than −10D and a refractive astigmatism less than −3D. The Bowman's layer in the central 3 mm cornea is imaged with high resolution optical coherence tomography (Envisu, Bioptigen Inc., Morrisville, USA). The optical coherence tomography exhibited a resolution of 2.4 μm in tissue, which allowed Bowman's layer image with sufficient number of pixels. The optical coherence tomography imaging is performed not only at 1 month but also at day 1 and week 1 after surgery to evaluate the longitudinal variation of the microdistortions.

The location of the 2-Dimensional (D) scan is set at each follow-up such that it subdivided the projection image of the cornea into nearly two equal halves. Further, at least three 2-D scans are acquired in quick succession at each follow-up time point.

The anterior edge of the Bowman's layer is segmented into number of pixels from the optical coherence tomography images before and after surgery using gradient based thresholding. After segmentation, a 3$^{rd}$ order polynomial is curve fit to the segmented pixels of the Bowman's layer edge.

The areas represent the areas enclosed between the microdistortions and curve fit. These areas in the segmented edge are represented as $A_1, A_2, A_3 \ldots A_n$, where n is the number of areas enclosed.

BRI is defined as the summation:

$$BRI = \sum_{k=1}^{n} A_k = A_1 + A_2 + \ldots + A_k$$

The mean BRI from the three images of each eye is calculated and used for further analyses.

The present invention employs fully automated image segmentation method to define BRI as an index of quantification of microdistortions using high resolution optical coherence tomography, which has a resolution of 2.4 μm in tissue and is advantageous over the existing methods. Further, the visual examination of microdistortions showed that they remain stable after 1 week and reduces marginally. The results also showed that the ratio of post to preoperative BRI correlated positively with the magnitude of refractive correction and change in visual acuity, which implies that the magnitude of microdistortions increased as more tissue is removed after SMILE. BRI quantifies the smoothness of the layer and is useful for regional analyses without the need for peripheral corneal imaging. BRI is useful for diagnosis of disease and prognosis of treatments in human.

In addition to Bowman's layer, the present invention is also useful to quantify the roughness of other layers of the cornea such as epithelium, stroma, Descemet's membrane, Dua's layer and endothelium in response to surgery or disease.

We claim:
1. A method of evaluating microdistortions in a Bowman's layer of a cornea, the method comprising:
   imaging the cornea using spectral domain optical coherence tomography to obtain an image that includes the anterior edge of the Bowman's layer;
   overlaying a smooth representation of the anterior edge of the Bowman's layer on the image of an anterior edge of the Bowman's layer;
   segmenting the anterior edge of a Bowman's layer of the cornea in the image into a selected number of pixels or voxels to obtain segmented areas of pixels or segmented volumes of voxels representing microdistortions of the Bowman's layer, each segmented area or volume being the area or volume above or below the anterior edge of the Bowman's layer to the smooth representation of the anterior edge of the Bowman's layer such that 3rd order polynomial is curve fit to the segmented areas of pixels or the segmented volumes of voxels of the anterior edge of the Bowman's layer;
   calculating Bowman's Roughness Index (BRI) based on the segmented areas of pixels or the segmented volumes of voxels; and
   comparing the calculated index to a previous index obtained from a previously taken image to evaluate relative changes in microdistortions of the Bowman's layer.
2. The method as claimed in claim 1, wherein BRI is calculated by analyzing the regional corneal imaging without the need for peripheral corneal imaging.

3. The method as claimed in claim 1, wherein the roughness of the Bowman's layer is analyzed by subjecting the Bowman's layer to 3-D mapping using the calculated BRI.

4. The method as claimed in claim 1, wherein BRI is useful as for diagnosis of diseases and prognosis for treatment of diseases in human.

\* \* \* \* \*